United States Patent
Farrugia et al.

(10) Patent No.: US 6,332,463 B1
(45) Date of Patent: Dec. 25, 2001

(54) FLOW ESTIMATION AND COMPENSATION OF FLOW-INDUCED PRESSURE SWINGS IN CPAP TREATMENT AND ASSISTED RESPIRATION

(75) Inventors: Steven Paul Farrugia, Bexley; Shane Darren Finn, North Rocks, both of (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 08/894,304

(22) PCT Filed: Sep. 13, 1996

(86) PCT No.: PCT/AU96/00580

§ 371 Date: Nov. 17, 1997

§ 102(e) Date: Nov. 17, 1997

(87) PCT Pub. No.: WO97/10019

PCT Pub. Date: Mar. 20, 1997

(30) Foreign Application Priority Data

Sep. 15, 1995 (AU) .......................................... 5478

(51) Int. Cl.⁷ .................................................. A61M 16/00
(52) U.S. Cl. ............................... 128/204.18; 128/204.21; 128/204.23
(58) Field of Search ...................... 128/204.18, 204.21, 128/204.23, 205.18

(56) References Cited

U.S. PATENT DOCUMENTS

| Re. 35,295 | 7/1996 | Estes et al. . |
| Re. 35,339 | 10/1996 | Rapoport . |
| 2,904,033 | 9/1959 | Shane . |
| 3,099,985 | 8/1963 | Wilson et al. .................. 128/203.11 |
| 3,502,100 | 3/1970 | Jonson . |

(List continued on next page.)

FOREIGN PATENT DOCUMENTS

| B-59270/90 | 12/1990 | (AU) . |
| A-62221/90 | 3/1991 | (AU) . |
| A-76019/91 | 1/1992 | (AU) . |
| A-33877/93 | 4/1993 | (AU) . |
| B-59270/90 | 5/1993 | (AU) . |

(List continued on next page.)

OTHER PUBLICATIONS

Derwent: Flowmeter for fluids–has turbine transducer and volumetric sensor for simultaneous calibration.
Mark Kantrowitz, Erik Horskotte and Cliff Joslyn; "Answers to Frequently Asked Questions about Fuzzy Logic and Fuzzy Expert Systems" Version 1.24 last Modified 20 2 96.
New! Breas PV 100 CPAP First Quality and Function. At the right Price; Jul. 4, 1998, pp 1–2.

(List continued on next page.)

Primary Examiner—Aaron J. Lewis
(74) Attorney, Agent, or Firm—Pillsbury Winthrop LLP (57) ABSTRACT

A method of flow estimation during CPAP treatment is disclosed and involves measuring turbine (32) speed by means of the motor's Hall-effect sensors (80). The equivalent pressure, $p_{est}$, that would be developed by the turbine (32) for the measured speed if the flow were zero is estimated using a predetermined mathematical function. Coincidentally with the speed measurement and pressure estimation, the delivery tube pressure, $p_{act}$, is measured by the pressure transducer (42), and from $p_{act}$ together with $p_{est}$, the difference between the two pressures is calculated, representing an estimation of flow, $f_{est}$. The flow estimation value can be linearised by the square root device (86), and then filtered by the combination of low pass and high pass filters (90, 92) to derive a filtered flow estimate value, that has the non-respiratory components removed. A method of flow compensation of flow-induced pressure swings also is disclosed.

11 Claims, 6 Drawing Sheets

U.S. PATENT DOCUMENTS

| | | |
|---|---|---|
| 3,559,638 | 2/1971 | Potter . |
| 3,595,228 | 7/1971 | Simon et al. . |
| 3,611,801 | 10/1971 | Paine et al. . |
| 3,726,270 | 4/1973 | Griffis et al. . |
| 3,741,208 | 6/1973 | Jonsson et al. ................ 128/204.23 |
| 3,783,893 | 1/1974 | Davison ........................... 137/527.8 |
| 3,802,417 | 4/1974 | Lang . |
| 3,817,246 | 6/1974 | Weigl . |
| 3,882,847 | 5/1975 | Jacobs . |
| 3,903,875 | 9/1975 | Hughes . |
| 3,914,994 | 10/1975 | Banner ................................. 73/118 |
| 3,932,054 | 1/1976 | McKelvey . |
| 3,985,467 | 10/1976 | Lefferson .............................. 417/20 |
| 3,989,037 | 11/1976 | Franetzki . |
| 3,992,598 | 11/1976 | Welsh et al. . |
| 3,995,661 | 12/1976 | Van Fossen ........................... 251/65 |
| 4,006,634 | 2/1977 | Billette et al. . |
| 4,083,245 | 4/1978 | Osborn . |
| 4,109,749 | 8/1978 | Sweet ................................. 181/230 |
| 4,119,096 | 10/1978 | Drews .............................. 128/200.16 |
| 4,206,754 | 6/1980 | Cox et al. ....................... 128/204.21 |
| 4,249,527 | 2/1981 | Ko et al. .......................... 128/204.18 |
| 4,301,833 | 11/1981 | Donald, III .......................... 137/521 |
| 4,312,235 | 1/1982 | Daigle . |
| 4,322,594 | 3/1982 | Brisson . |
| 4,381,788 | 5/1983 | Douglas . |
| 4,387,722 | 6/1983 | Kearns . |
| 4,396,034 | 8/1983 | Cherniak ............................. 137/514 |
| 4,414,982 | 11/1983 | Durkan ................................ 600/529 |
| 4,433,693 | 2/1984 | Hochstein . |
| 4,448,058 | 5/1984 | Jaffe et al. .............................. 73/23 |
| 4,449,525 | 5/1984 | White et al. .................... 128/203.11 |
| 4,481,944 | 11/1984 | Bunnell .......................... 128/204.18 |
| 4,499,914 | 2/1985 | Schebler ............................. 137/81.1 |
| 4,506,666 | 3/1985 | Durkan ............................ 128/204.23 |
| 4,519,399 | 5/1985 | Hori ..................................... 600/537 |
| 4,530,334 | 7/1985 | Pagdin ................................ 123/494 |
| 4,550,615 | 11/1985 | Grant . |
| 4,550,726 | 11/1985 | McEwen . |
| 4,558,710 | 12/1985 | Eichler ................................. 600/532 |
| 4,570,631 | 2/1986 | Durkan . |
| 4,576,179 | 3/1986 | Manus et al. . |
| 4,579,114 | 4/1986 | Gray et al. ..................... 128/203.11 |
| 4,580,575 | 4/1986 | Birnbaum et al. . |
| 4,592,880 | 6/1986 | Murakami .............................. 264/22 |
| 4,595,016 | 6/1986 | Fertig et al. . |
| 4,602,644 | 7/1986 | DiBenedetto et al. . |
| 4,630,614 | 12/1986 | Atlas ..................................... 600/534 |
| 4,648,396 | 3/1987 | Raemer . |
| 4,648,407 | 3/1987 | Sackner ................................ 600/534 |
| 4,655,213 | 4/1987 | Rapoport et al. . |
| 4,677,975 | 7/1987 | Edgar et al. .................... 128/200.14 |
| 4,686,974 | 8/1987 | Sato et al. . |
| 4,686,999 | 8/1987 | Snyder et al. ....................... 600/529 |
| 4,738,266 | 4/1988 | Thatcher . |
| 4,747,403 | 5/1988 | Gluck et al. ..................... 128/204.21 |
| 4,773,411 | 9/1988 | Downs ............................. 128/204.18 |
| 4,777,963 | 10/1988 | McKenna . |
| 4,795,314 | 1/1989 | Prybella et al. ....................... 417/43 |
| 4,802,485 | 2/1989 | Bowers, et al. . |
| 4,803,471 | 2/1989 | Rowland ............................... 340/626 |
| 4,819,629 | 4/1989 | Jonson ............................. 128/203.22 |
| 4,823,788 | 4/1989 | Smith et al. .................... 128/205.24 |
| 4,825,802 | 5/1989 | Le Bec ................................... 116/70 |
| 4,827,922 | 5/1989 | Champain et al. .............. 128/204.21 |
| 4,838,258 | 6/1989 | Dryden et al. . |
| 4,844,085 | 7/1989 | Gattinoni . |
| 4,856,506 | 8/1989 | Jinotti ............................... 128/203.11 |
| 4,860,766 | 8/1989 | Sackner . |
| 4,870,960 | 10/1989 | Hradek ............................ 128/202.22 |
| 4,870,963 | 10/1989 | Carter ............................. 128/205.24 |
| 4,887,607 | 12/1989 | Beatty . |
| 4,913,401 | 4/1990 | Handke . |
| 4,915,103 | 4/1990 | Visveshwara et al. ......... 128/204.23 |
| 4,928,684 | 5/1990 | Breitenfelder et al. ......... 128/204.21 |
| 4,938,210 | 7/1990 | Shene .............................. 128/203.12 |
| 4,938,212 | 7/1990 | Snook et al. . |
| 4,944,310 | 7/1990 | Sullivan . |
| 4,957,107 | * 9/1990 | Sipin ............................... 128/204.21 |
| 4,960,118 | 10/1990 | Pennock . |
| 4,971,065 | 11/1990 | Pearce . |
| 4,972,842 | 11/1990 | Korten et al. ......................... 600/529 |
| 4,982,738 | 1/1991 | Griebel . |
| 4,986,269 | 1/1991 | Hakkinen ........................ 128/204.23 |
| 4,989,599 | 2/1991 | Carter ............................. 128/207.18 |
| 5,024,219 | 6/1991 | Dietz . |
| 5,046,491 | 9/1991 | Derrick ........................... 128/200.24 |
| 5,048,515 | 9/1991 | Sanso .............................. 128/204.26 |
| 5,052,400 | 10/1991 | Dietz . |
| 5,063,922 | 11/1991 | Hakkinen ........................ 128/200.16 |
| 5,063,938 | 11/1991 | Beck et al. ............................ 600/537 |
| 5,065,756 | 11/1991 | Rapoport . |
| 5,069,222 | 12/1991 | McDonald, Jr. . |
| 5,090,248 | 2/1992 | Cimmino et al. . |
| 5,099,635 | 3/1992 | Scarberry . |
| 5,099,837 | 3/1992 | Russel, Sr. et al. ............. 128/204.26 |
| 5,105,354 | 4/1992 | Nishimura . |
| 5,107,830 | 4/1992 | Younes ............................ 128/204.18 |
| 5,107,831 | 4/1992 | Halpern et al. ................. 128/204.26 |
| 5,117,819 | 6/1992 | Servidio et al. . |
| 5,129,390 | 7/1992 | Chopin et al. ................... 128/204.21 |
| 5,134,995 | 8/1992 | Gruenke et al. . |
| 5,148,802 | 9/1992 | Sanders et al. . |
| 5,161,525 | 11/1992 | Kimm et al. . |
| 5,161,541 | 11/1992 | Bowman et al. . |
| 5,165,398 | 11/1992 | Bird ................................. 128/204.25 |
| 5,170,798 | 12/1992 | Riker . |
| 5,174,287 | 12/1992 | Kallok et al. .................... 128/200.24 |
| 5,178,138 | 1/1993 | Walstrom et al. ............... 128/200.23 |
| 5,183,983 | 2/1993 | Knop . |
| 5,190,048 | 3/1993 | Wilkinson . |
| 5,195,528 | 3/1993 | Hok . |
| 5,199,424 | 4/1993 | Sullivan et al. . |
| 5,203,343 | 4/1993 | Axe et al. . |
| 5,230,330 | 7/1993 | Price ............................... 128/203.11 |
| 5,231,979 | 8/1993 | Rose et al. . |
| 5,231,983 | 8/1993 | Matson et al. ................... 128/207.14 |
| 5,233,983 | 8/1993 | Markowitz ............................ 607/42 |
| 5,239,994 | 8/1993 | Atkins ............................. 128/204.18 |
| 5,239,995 | * 8/1993 | Estes et al. ...................... 128/204.21 |
| 5,245,995 | 9/1993 | Sullilvan et al. . |
| 5,259,373 | 11/1993 | Gruenke et al. . |
| 5,271,391 | 12/1993 | Graves . |
| 5,280,784 | 1/1994 | Kohler ............................. 128/200.14 |
| 5,293,864 | 3/1994 | McFadden ....................... 128/201.29 |
| 5,295,491 | 3/1994 | Gevins ................................. 600/544 |
| 5,303,698 | 4/1994 | Tobia et al. ..................... 128/204.21 |
| 5,303,700 | 4/1994 | Weismann et al. .............. 128/204.23 |
| 5,305,787 | 4/1994 | Thygesen ............................. 137/527 |
| 5,311,875 | 5/1994 | Stasz . |
| 5,313,937 | 5/1994 | Zdrojkowski . |
| 5,322,057 | 6/1994 | Raabe et al. ..................... 128/203.12 |
| 5,327,899 | 7/1994 | Harris et al. . |
| 5,335,654 | 8/1994 | Rapoport . |
| 5,335,656 | 8/1994 | Bowe et al. ..................... 128/207.18 |
| 5,343,878 | 9/1994 | Scarberry et al. . |
| 5,353,788 | 10/1994 | Miles . |
| 5,360,008 | 11/1994 | Campbell, Jr. . |
| 5,373,842 | 12/1994 | Olsson et al. ................... 128/204.21 |
| 5,388,571 | 2/1995 | Roberts et al. ................. 128/203.12 |
| 5,394,882 | 3/1995 | Mawhinney . |

| | | | |
|---|---|---|---|
| 5,398,673 | 3/1995 | Lambert | 128/203.28 |
| 5,400,777 | 3/1995 | Olsson et al. | 128/204.18 |
| 5,404,871 | 4/1995 | Goodman et al. | 128/200.14 |
| 5,413,111 | 5/1995 | Wilkinson | 600/537 |
| 5,433,193 | 7/1995 | Sanders et al. . | |
| 5,438,980 | 8/1995 | Phillips | 128/204.23 |
| 5,443,061 | 8/1995 | Champain et al. . | |
| 5,443,075 | 8/1995 | Holscher | 600/538 |
| 5,458,137 | 10/1995 | Axe et al. . | |
| 5,479,920 | 1/1996 | Piper et al. | 128/204.23 |
| 5,479,939 | 1/1996 | Ogino . | |
| 5,483,969 | 1/1996 | Testerman et al. . | |
| 5,490,502 | 2/1996 | Rapoport et al. . | |
| 5,492,113 | 2/1996 | Estes et al. . | |
| 5,503,146 | 4/1996 | Froehlich et al. . | |
| 5,507,282 | 4/1996 | Younes . | |
| 5,509,404 | 4/1996 | Lloyd et al. | 128/200.14 |
| 5,509,414 | 4/1996 | Hok | 600/534 |
| 5,513,631 | 5/1996 | McWilliams . | |
| 5,517,983 | 5/1996 | Deighan et al. . | |
| 5,522,382 | 6/1996 | Sullivan et al. . | |
| 5,526,805 | 6/1996 | Lutz et al. | 128/204.18 |
| 5,535,738 | 7/1996 | Estes et al. . | |
| 5,535,739 | 7/1996 | Rapoport et al. . | |
| 5,537,997 | 7/1996 | Mechlenburg et al. . | |
| 5,540,219 | 7/1996 | Mechlenburg et al. . | |
| 5,540,220 | 7/1996 | Gropper et al. | 128/204.23 |
| 5,540,733 | 7/1996 | Testerman et al. . | |
| 5,546,933 | 8/1996 | Rapoport et al. | 128/204.23 |
| 5,546,952 | 8/1996 | Erickson . | |
| 5,546,993 | 8/1996 | Rapoport et al. . | |
| 5,549,106 | 8/1996 | Gruenke et al. | 128/204.23 |
| 5,549,655 | 8/1996 | Erickson . | |
| 5,551,418 | 9/1996 | Estes et al. . | |
| 5,551,419 | 9/1996 | Froehlich et al. . | |
| 5,558,099 | 9/1996 | Bowman et al. . | |
| 5,567,127 | 10/1996 | Wentz | 417/312 |
| 5,570,682 | 11/1996 | Johnson | 128/200.14 |
| 5,577,496 * | 11/1996 | Blackwood et al. | 128/204.21 |
| 5,588,439 | 12/1996 | Hollub . | |
| 5,598,838 | 2/1997 | Servidio et al. . | |
| 5,605,151 | 2/1997 | Lynn . | |
| 5,608,647 | 3/1997 | Rubsamen et al. | 128/204.18 |
| 5,617,846 | 4/1997 | Graetz et al. | 128/204.21 |
| 5,630,411 | 5/1997 | Holscher | 128/205.24 |
| 5,632,269 | 5/1997 | Zdrojkowski . | |
| 5,633,552 | 5/1997 | Lee et al. | 310/311 |
| 5,642,730 | 7/1997 | Baran | 128/207.14 |
| 5,645,053 | 7/1997 | Remmers et al. | 128/204.23 |
| 5,645,054 | 7/1997 | Cotner et al. . | |
| 5,647,351 | 7/1997 | Wesimann et al. | 128/204.21 |
| 5,655,520 | 8/1997 | Howe et al. | 128/203.12 |
| 5,655,522 | 8/1997 | Mechlenburg et al. . | |
| 5,660,171 | 8/1997 | Kimm et al. | 128/204.23 |
| 5,666,946 | 9/1997 | Langenback | 128/200.16 |
| 5,682,878 | 11/1997 | Ogden | 128/204.23 |
| 5,685,296 | 11/1997 | Zdrojkowski et al. | 128/205.24 |
| 5,694,926 * | 12/1997 | Devries et al. | 128/204.21 |
| 5,701,883 | 12/1997 | Hete et al. | 128/204.26 |
| 5,704,345 * | 1/1998 | Berthon-Jones | 128/204.21 |
| 5,715,812 | 2/1998 | Deighan et al. | 128/204.23 |
| 5,730,121 | 3/1998 | Hawkins, Jr. et al. | 128/205.25 |
| 5,740,795 * | 4/1998 | Brydon | 128/204.21 |
| 5,794,615 | 8/1998 | Estes | 128/204.23 |
| 5,797,852 | 8/1998 | Karakasoglu et al. | 600/529 |
| 5,803,066 * | 9/1998 | Rapoport et al. | 128/204.21 |
| 5,823,187 | 10/1998 | Estes et al. | 128/204.23 |
| 5,845,636 | 12/1998 | Gruenke et al. | 128/204.23 |
| 6,009,871 * | 1/2000 | Kiske et al. | 128/204.21 |

FOREIGN PATENT DOCUMENTS

| | | |
|---|---|---|
| A-48748/93 | 9/1993 | (AU) . |
| A-52628/93 | 7/1994 | (AU) . |
| B 79174/94 | 6/1995 | (AU) . |
| A-34471/95 | 2/1996 | (AU) . |
| A-40711-95 | 4/1996 | (AU) . |
| B 34354/95 | 5/1996 | (AU) . |
| A 39130/95 | 6/1996 | (AU) . |
| 459104 | 4/1928 | (DE) . |
| 34 02 603 A1 | 1/1984 | (DE) . |
| 3345067 A1 | 6/1984 | (DE) . |
| 3429345 A1 | 6/1985 | (DE) . |
| 3537507 A1 | 4/1987 | (DE) . |
| 3539073 A1 | 5/1987 | (DE) . |
| WO 94/16759 | 8/1994 | (DE) . |
| 4432219 C1 | 4/1996 | (DE) . |
| 296 12 119 U1 | 12/1996 | (DE) . |
| 195 36 632 A1 | 3/1997 | (DE) . |
| 0 066 451 A1 | 12/1982 | (EP) . |
| B1 0 088 761 | 9/1983 | (EP) . |
| 0 164 500 A2 | 3/1985 | (EP) . |
| 0 171 321 A1 | 2/1986 | (EP) . |
| 0 185 980 | 7/1986 | (EP) . |
| 0 236 850 A2 | 9/1987 | (EP) . |
| 0 872 643 A2 | 3/1988 | (EP) . |
| 298 367 A2 | 1/1989 | (EP) . |
| 0 425 092 A1 | 9/1989 | (EP) . |
| 0 452 001 A2 | 3/1990 | (EP) . |
| 0388 525 A1 | 9/1990 | (EP) . |
| 0 425 092 A1 | 5/1991 | (EP) . |
| 0 461 281 A1 | 12/1991 | (EP) . |
| 0 481 459 A1 | 4/1992 | (EP) . |
| 481 459 A1 | 4/1992 | (EP) . |
| 0 062 166 A2 | 10/1992 | (EP) . |
| 0549299 A2 | 6/1993 | (EP) . |
| 606 687 A2 | 7/1994 | (EP) . |
| 0705615 A1 | 9/1994 | (EP) . |
| 0 714 670 A2 | 12/1994 | (EP) . |
| 0651971 A1 | 5/1995 | (EP) . |
| 0 656 216 A2 | 6/1995 | (EP) . |
| 0 661 071 A1 | 7/1995 | (EP) . |
| 178 925 A2 | 4/1996 | (EP) . |
| 0 709 107 A1 | 5/1996 | (EP) . |
| 0 714 670 A2 | 6/1996 | (EP) . |
| 0 765 631 A2 | 4/1997 | (EP) . |
| 0 788 805 A2 | 8/1997 | (EP) . |
| 0 839 545 A1 | 5/1998 | (EP) . |
| 2 574 657 A1 | 6/1986 | (FR) . |
| 2 672 221 A1 | 8/1992 | (FR) . |
| 2682042 A1 | 4/1993 | (FR) . |
| 1 444 053 | 7/1976 | (GB) . |
| 1583273 | 1/1981 | (GB) . |
| 2 077 444 A | 12/1981 | (GB) . |
| 2 147 506 A | 5/1985 | (GB) . |
| 2 164 569 A | 3/1986 | (GB) . |
| 2 166 871 A | 5/1986 | (GB) . |
| 2 205 167 A | 11/1988 | (GB) . |
| 2 221 302 A | 1/1990 | (GB) . |
| 2 254 700 A | 10/1992 | (GB) . |
| 2 261 290 A | 5/1993 | (GB) . |
| 2 271 811 A | 4/1994 | (GB) . |
| 1432572 | 4/1996 | (GB) . |
| 2 294 400 A | 5/1996 | (GB) . |
| 54-104369 | 8/1979 | (JP) . |
| 60-212607 | 10/1985 | (JP) . |
| 62-103297 | 4/1987 | (JP) . |
| 63-270026 A | 4/1987 | (JP) . |
| 63-270027 A | 4/1987 | (JP) . |
| 63-270028 A | 4/1987 | (JP) . |

| | | |
|---|---|---|
| 63-275352 | 11/1988 | (JP) . |
| 2-173397 | 12/1988 | (JP) . |
| 4-70516 | 3/1992 | (JP) . |
| 4-70516 A | 3/1992 | (JP) . |
| 06249741 A | 9/1994 | (JP) . |
| 07280609 A | 10/1995 | (JP) . |
| 8019610 A | 1/1996 | (JP) . |
| 1710064 A1 | 2/1992 | (SE) . |
| 467041 B | 5/1992 | (SE) . |
| WO 82/03326 | 10/1982 | (WO) . |
| WO 82/03548 | 10/1982 | (WO) . |
| WO 86/05965 | 10/1986 | (WO) . |
| WO 86/06969 | 12/1986 | (WO) . |
| WO 87/02577 | 5/1987 | (WO) . |
| WO 89/09565 | 10/1988 | (WO) . |
| WO 88/10108 | 12/1988 | (WO) . |
| WO 90/09146 | 8/1990 | (WO) . |
| WO 90/14121 | 11/1990 | (WO) . |
| WO 91/12051 | 8/1991 | (WO) . |
| WO 92/11054 | 7/1992 | (WO) . |
| WO 92/15353 | 9/1992 | (WO) . |
| WO 92/22244 | 12/1992 | (WO) . |
| WO 93/08857 | 5/1993 | (WO) . |
| WO 93/09834 | 5/1993 | (WO) . |
| WO 93/21982 | 11/1993 | (WO) . |
| WO 93/24169 | 12/1993 | (WO) . |
| WO 94/04071 | 3/1994 | (WO) . |
| WO 94/20018 | 9/1994 | (WO) . |
| WO 94/20051 | 9/1994 | (WO) . |
| WO 94/22517 | 10/1994 | (WO) . |
| WO 94/23780 | 10/1994 | (WO) . |
| WO 95/32016 | 11/1995 | (WO) . |
| WO 96/16688 | 6/1996 | (WO) . |
| WO 96/32055 | 10/1996 | (WO) . |
| WO 96/36279 | 11/1996 | (WO) . |
| WO 96/40337 | 12/1996 | (WO) . |
| WO 96/41571 | 12/1996 | (WO) . |
| WO 97/02064 | 1/1997 | (WO) . |
| WO 97/05824 | 2/1997 | (WO) . |
| WO 97/10019 | 3/1997 | (WO) . |
| WO 97/10868 | 3/1997 | (WO) . |
| WO 97/14354 | 4/1997 | (WO) . |
| WO 97/15343 | 5/1997 | (WO) . |
| WO 97/18752 | 5/1997 | (WO) . |
| WO 97/20499 | 6/1997 | (WO) . |
| WO 97/22377 | 6/1997 | (WO) . |
| WO 97/28838 | 8/1997 | (WO) . |
| WO 97/41812 | 11/1997 | (WO) . |
| WO 95/34917 | 12/1997 | (WO) . |
| WO 98/06449 | 2/1998 | (WO) . |
| WO 98/25662 | 6/1998 | (WO) . |
| WO 98/33433 | 8/1998 | (WO) . |
| WO 98/35715 | 8/1998 | (WO) . |
| WO 98/36245 | 8/1998 | (WO) . |
| WO 98/36338 | 8/1998 | (WO) . |
| WO 98/47554 | 10/1998 | (WO) . |
| WO 98/57691 | 12/1998 | (WO) . |

OTHER PUBLICATIONS

PV 101 Bi Level CPAP and PV 102 Bi–Level Time; pp 1–3.
Prodigy Medical Supplies Co. Ltd.; CPAP.
Puritan Bennett; Companion 318 Nasal CPAP System; 5/93.
Nellcor Puritan Bennett; Announcing the Goodnight 314 and GoodKnight 318 Nasal CPAP Systems.
Puritan Bennett; Clean, Quiet, and Comfortable . . . The Companion's 515 Nasal CPAP System; 6/88.
DeVilbiss Night Guard Nasal CPAP for the Treatment of Obstructive Sleep Apnea.
Sunrise; DeVilbiss Horizon LT 8001 Nasal CPAP Therapy Small in Size, big features.
Devilbiss; Revitalizer Soft Start; The Facts Speak for Themselves.
Tranquility; Performance CPAP Advantage.
Healthdyne International; Tranquility Plus.
Respironics Inc.; Respironics' Solo CPAP System Provides Simplified OSA Therapy at an Outstanding value; Sep. 19, 1996.
Respironics Inc.; The First Family of OSA Therapy; 1991.
Fisher & Paykel Healthcare; HC200 Series Nasal CPAP Blower & Heated Humidifier.
Pierre Medical; Morphee Plus appareil de traitment des apnees du sommeil manuel d'utilisation.
Weinmann:Hamburg; Somnotron nCPAP–Great WM 2300.
Puritan Bennett; 515a Part of our Blueprint for the Future; 3/90.
Puritan Bennett; Companion 320 I/E Bi–Level Respiratory System; 4/93.
ResMed; Sullivan VPAP II & II ST.
ResMed; The Sullivan V Family of CPAP Systems.
ResMed; The AutoSet Portable II.
ResMed; Sullivan Nasal CPAP System.
ResMed; The Sullivan IIID.
ResMed; The Sulliavan Comfort.
DeVilbiss a Division of Sunrise Medical; Expand your Horizons With The Horizons.
Healthdyne Technologies; Home Health Care Dealer; The Journal of Home Medical Equipment and Services/Supplier; Nov. and Dec. 1997.
Healthdyne International; Tranquility Quest, The Compact CPAP for Greater patient comfort.
AirStep; Medical Products . . . Stand the Test of Time.
MAP Medical Progress for Physician und Patient; The Gentle Therapy for Sleep–Related Breathing Disorders.
Taema; Ventilation CP 90.
DPAP; Breath, by breath, by breath.
Lifecare; Smallest. Quietest. Smartest.
Lifecare; Quiet CPAP System for Maxium Compliance; 1991.
Lifecare; Software Nasal Mask, Custom Nasal Masks; 1991.
Nidek Medical; Silenzio.
Weinmann; Just to Fell Well, Sensitive Sleep Apnoea Therapy with Somnotron 3 and Somno–Mask System.
Respironics Inc.; Aria CPAP System.
Respironics Inc.; SleepEasy III A New Dawn in Patient Compliance.
Respironics Inc.; Muliple Choice REMstar Choice Nasal CPAP System.
MaxII nCPAP and Moritz II Bi–Level Brochure.

* cited by examiner

FLOW ESTIMATION AND COMPENSATION OF FLOW-INDUCED PRESSURE SWINGS IN CPAP TREATMENT AND ASSISTED RESPIRATION

FIELD OF THE INVENTION

This invention relates to methods and apparatus for the estimation of respiratory flow, and to the compensation of pressure swings at the entrance of a patient's airway induced by respiratory flow in the course of continuous positive airway pressure (CPAP) treatment or assisted respiration.

BACKGROUND OF THE INVENTION

The administration of CPAP is common in the treatment of Obstructive Sleep Apnea (OSA) syndrome and Upper Airway Resistance syndrome. CPAP treatment effectively acts as a pneumatic splint of a patient's upper airway by providing air or breathable gas at a pressure elevated above atmospheric pressure to the entrance of the patient's airway. Treatment pressures in the range 4–20 cm $H_2O$ are commonly encountered. More sophisticated forms of CPAP include bi-level CPAP in which different treatment pressures are applied in synchronism with the inspiratory and expiratory phases of respiration, and autosetting (controlled variable treatment pressure) CPAP, as described in U.S. Pat. No. 5,245,995. In all forms of CPAP treatment it is desired to maintain the treatment pressure, usually clinically determined by a physician, to be as constant as possible to maintain treatment efficacy without causing the patient undue discomfort by having to work against an unnecessarily high positive airway pressure.

Common to all forms of CPAP apparatus is a mask worn b a patient having connection via a flexible air delivery tube to a flow generator. The flow generator has a turbine driven by an electric motor that is under the control of a microprocessor-based controller.

In this specification a reference to a "mask" is to be understood as including a nose mask, a mouth mask, a nose and mouth mask in combination or a full face mask.

Simple CPAP machines estimate the mask pressure from the motor speed and operate under speed regulation. More sophisticated machines incorporate a pneumatic pressure transducer that provides a feedback signal representative of pressure at either the mask or a point within the flow generator itself. If the pressure feedback signal is from the mask, additional tubing or wires must extend between the mask and the flow generator which can give rise to sterilisation and/or safety problems. If pressure feedback is from a point within the flow generator, or at some other point removed from the mask, the impedance of the air delivery tube can result in flow-induced pressure swings at the mask. The pressure swings can be up to +5% of treatment pressure, and since it is desired to provide the patient with the minimum treatment pressure to provide treatment efficacy and yet avoid the patient doing unnecessary work during exhalation, these pressure swings are undesirable and should be eliminated as far as possible.

It is also desirable to be able to accurately determine dynamic air flow in the delivery tube and mask. "Flow" is to be understood as including both ventilation volume and a volumetric flow rate. The flow will have a component due to the flow generator that is modulated by patient respiration. The measurement of air flow in the air delivery tube can beneficially be used to measure the average volume breathed by the patient and to determine whether the patient is inhaling (inspiring) or exhaling (expiring), the latter of which is crucial in the implementation of bi-level CPAP. Currently this is done using an in-line sensor to directly measure flow, or by measuring the pressure drop across a restriction in the air delivery tube (or alternatively, the pressure drop alone the air delivery tube). These methods require the use of additional transducers, and in some cases additional wiring or tubing to connect the transducer to an appropriate point in the control circuitry of the CPAP apparatus.

It thus also is desirable to accurately measure or estimate air flow from the stand-point of enabling advanced control over the administration of CPAP treatment and ensuring efficacy of treatment and patient compliance without reducing patient comfort.

The present invention is directed to overcoming or at least ameliorating one or more of the foregoing problems.

SUMMARY OF THE INVENTION

In one broad form, the invention discloses a method to estimate gas flow from a turbine, the method comprising the steps of:
measuring the pressure of the gas flowing from the turbine when operating at a known rotational speed;
estimating the pressure of gas that would be delivered by said turbine at the known rotational speed if there was no flow; and
calculating the difference between the measured pressure and the estimated pressure to estimate the gas flow.

In another broad form, the invention discloses a method to estimate the flow of breathable gas to a patient from a flow generator having a turbine in the administration of continuous positive airway pressure (CPAP) treatment or assisted respiration, the method comprising the steps of:
measuring the pressure of gas ($p_{act}$) from the flow generator;
measuring the rotational speed ($\omega$) of the turbine;
estimating the pressure of gas ($p_{est}$) that would be delivered by the flow generator at the measured rotational speed if there were no flow to the patient: and
calculating the difference between $p_{est}$ and $p_{act}$ to give the estimate of flow ($f_{est}$).

The said difference further can be signal-processed to give a direct estimate of flow. The processing can include filtering to give a direct estimate of flow.

The invention yet further discloses a method to reduce flow-induced pressure swings at a patient mask during the administration of CPAP treatment or assisted respiration, said mask being coupled to a flow generator by a gas delivery tube and the pressure of delivered gas being measured at a point remote from said mask, said measured pressure being used to derive a treatment pressure control signal supplied to said flow generator to control said desired treatment pressure, the method comprising the steps of:
determining the flow of gas to the patient;
scaling said determined flow; and
adjusting said treatment pressure control signal by said scaled flow.

The scaled flow can be further filtered to pass only the scaled flow corresponding to increases in flow, corresponding to a reduction in the desired treatment pressure.

The invention yet further discloses apparatus to estimate the flow of gas from a flow generator turbine supplying breathable gas in CPAP treatment or assisted respiration, the apparatus comprising:
pressure measurement means for measuring the pressure of gas from the turbine when operating at a known rotational speed;

pressure estimation means for estimating the pressure of gas that would be delivered by said turbine at the known rotation speed if there was no flow; and processor means for calculating the difference between the measured pressure and the estimated pressure to give an estimation of flow.

The invention yet further discloses apparatus to provide CPAP treatment or assisted respiration for supplying a positive treatment pressure of breathable gas at the entrance of a patient's airway, the apparatus comprising:

a flow generator having a turbine:

a gas delivery tube connected at one end thereof with the flow generator;

a patient mask connected to the other end of the delivery tube to be worn by the patient;

pressure sensor means sensing delivery pressure from either the flow generator or the delivery tube remote from the mask; and processor means for controlling the flow generator, and further operable to estimate the flow of breathable gas by estimating the pressure of gas that would be delivered by the flow generator at the actual turbine rotational speed for zero flow and calculating the difference between the measured pressure and said estimated pressure to give an estimate of flow.

The apparatus can be further operable to scale the flow and compensate said pressure control signal by the scaled flow. The said difference further can be signal processed to give a direct estimate of flow. The processing can include filtering to remove non-respiratory components.

DETAILED DESCRIPTION OF PREFERRED EMBODIMENTS AND BEST MODE

The embodiments described relate to CPAP treatment apparatus, however it is to be understood that the invention equally has application in apparatus for the provision of assisted respiration or ventilation.

Flow Estimation

Figure 1:
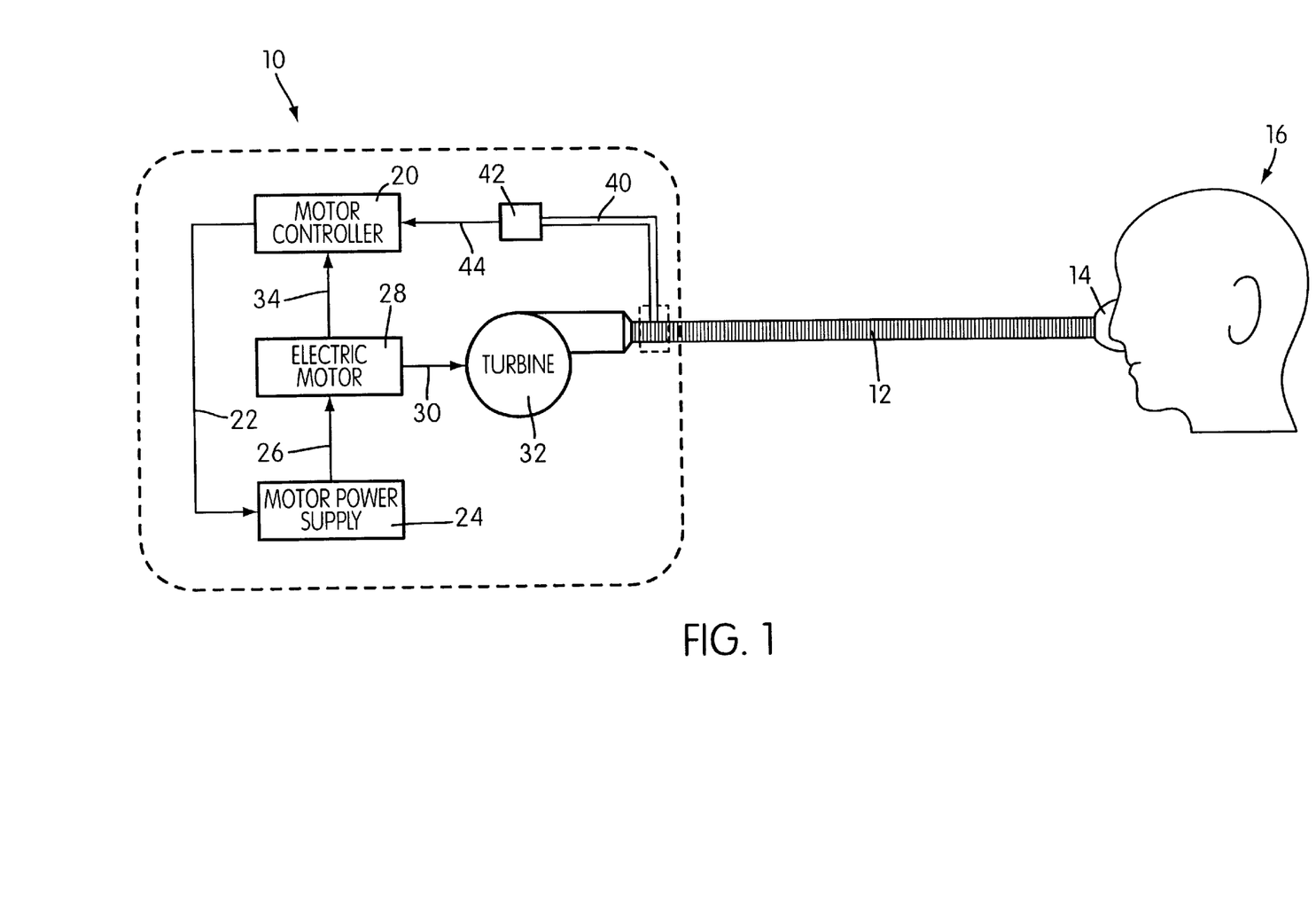
FIG. 1 is a schematic block diagram of CPAP treatment apparatus.

As shown in FIG. 1, the CPAP flow generator 10 is coupled to an air (or breathable gas) delivery tube 12, in turn coupled with a nose mask 14 being worn by a patient 16. The flow generator 10 comprises a microprocessor-based motor controller 20 that in one preferred form can include a 8-bit micro-controller such as the Motorola™ MC68HC805B6. The motor controller 20 is connected with an electric motor power supply 24 by a control line 22. The power supply 24 provides a supply of electrical energy, in the preferred form being DC, to the electrical motor 28 by a supply line 26. The electrical motor 28 is connected with a turbine 32 by a mechanical coupling 30. The electric motor 28 also is connected to the motor controller 20 by a signal line 34.

The turbine 32 provides breathable gas (including air) to the delivery tube 12 at a pressure elevated above atmospheric, and at a flow rate to satisfy a patient's treatment and respiration needs. This is achieved by speed control of the electric motor 28 and depended upon the pneumatic capacity of the turbine 32. The electric motor 28 preferably is a brushless DC type, such as the PAPST™ ECA 27-11. This motor has integral Hall-effect sensors that provide an electrical signal representative of motor speed provided to the motor controller 20 on the signal line 34. The electric motor 28 can alternatively have connected to it an optical or mechanical tachometer or any other convenient rotational speed-sensing device. The speed of a DC motor is directly proportional to the armature voltage as provided by the motor power supply 24. There is a relationship between motor speed, turbine delivery pressure and flow that can be determined by experimentation.

In the bi-level form of CPAP, the separate inspiratory and expiratory treatment pressures are achieved by rapid turbine speed control, although the use of solenoid-operated spill valves also is known in the art.

A pressure sensing tube 40 is connected with the air delivery tube 12 at a point proximate the exit of the turbine 32 within the casino of the flow generator 10. The sensing tube 40 is connected with a pressure transducer 42 resulting in an electrical signal indicative of turbine delivery pressure being passed to the motor controller 20 on a signal line 44.

The flow generator 10, including the pressure sensing tube 40 and pressure transducer 42, is commercially available as the present applicant's Sullivan™ III CPAP machine.

The pressure sensing tube 40 can alternatively be ported into the delivery tube 12 at any point along the length of that tube, or be ported into the mask 14 itself. It further is possible for the pressure transducer 42 to be proximate the delivery tube 12 so that there is only a small length of tubing from a port into the delivery tube 12 to the transducer 42, with the signal line 44 thus extending out of the casing of the flow generator 10.

Figure 2:
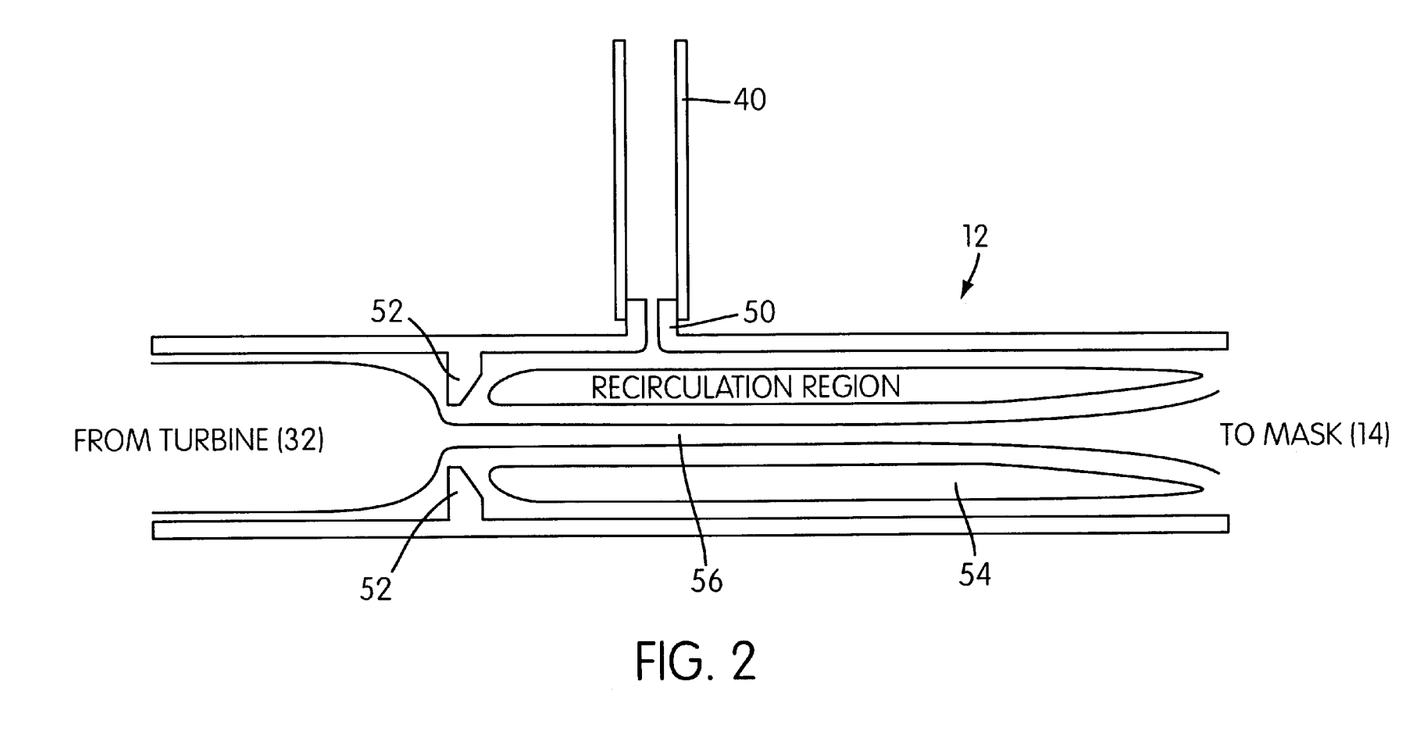
FIG. 2 is a cross-sectional view of the air delivery tube at the point where pressure is sensed.

FIG. 2 shows, in cross-section, detail of the region of the delivery tube 12 to which the pressure sensing tube 40 connects. The pressure sensing tube 40 attaches a pressure sensing port 50 located downstream of an orifice plate 52. The orifice plate represents an impedance that introduces a local pressure disturbance resulting in an air recirculation region 54 and a laminar flow region 56 extending downstream from the orifice plate 52. The pressure sensing port 50 is located in the recirculation region 54. Such a pneumatic recirculation also can be achieved by a localised reduction in the diameter of the air delivery tube 12.

Figure 3:
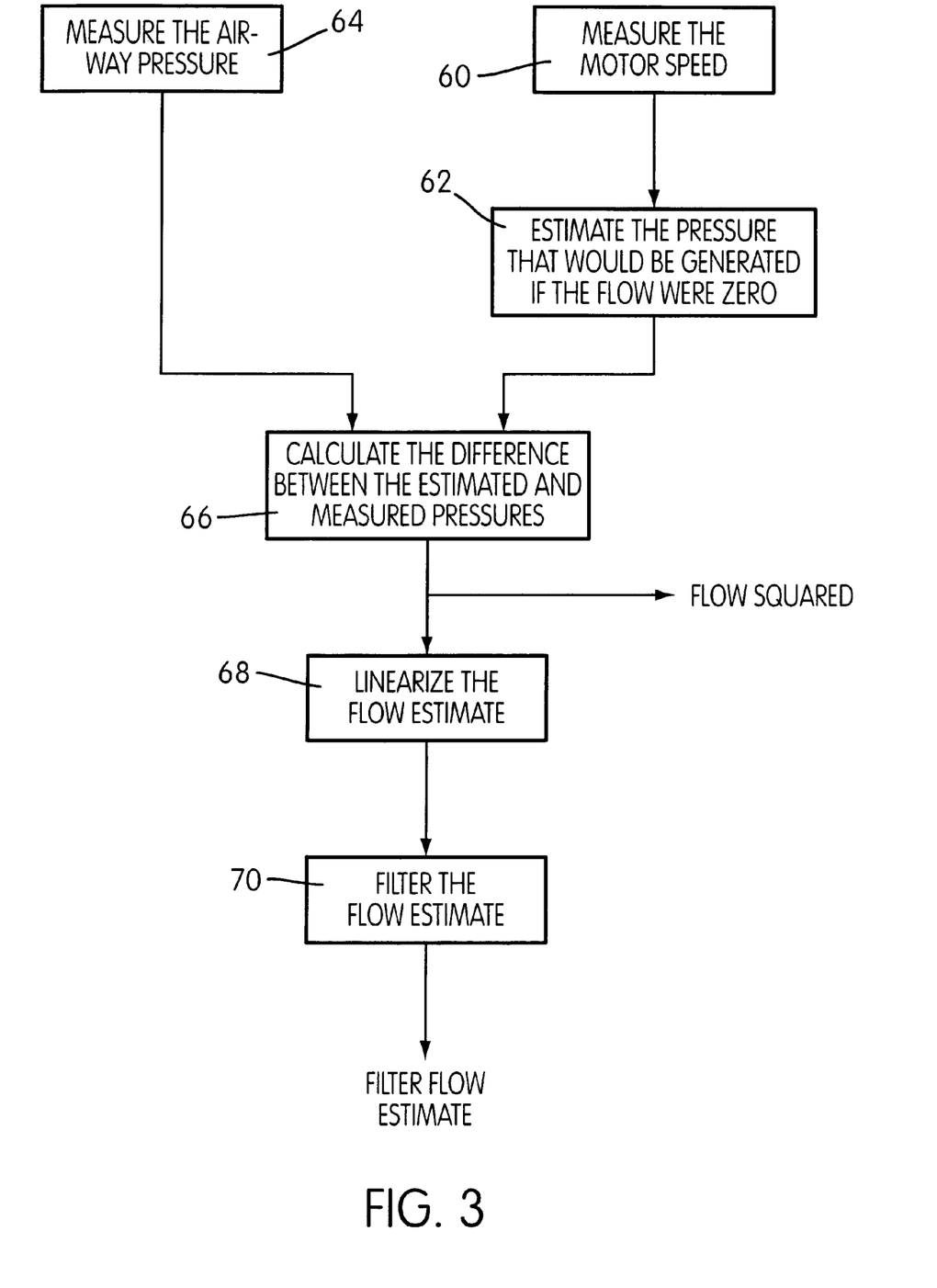
FIG. 3 is a block flow diagram describing the estimation of flow.
Figure 4:
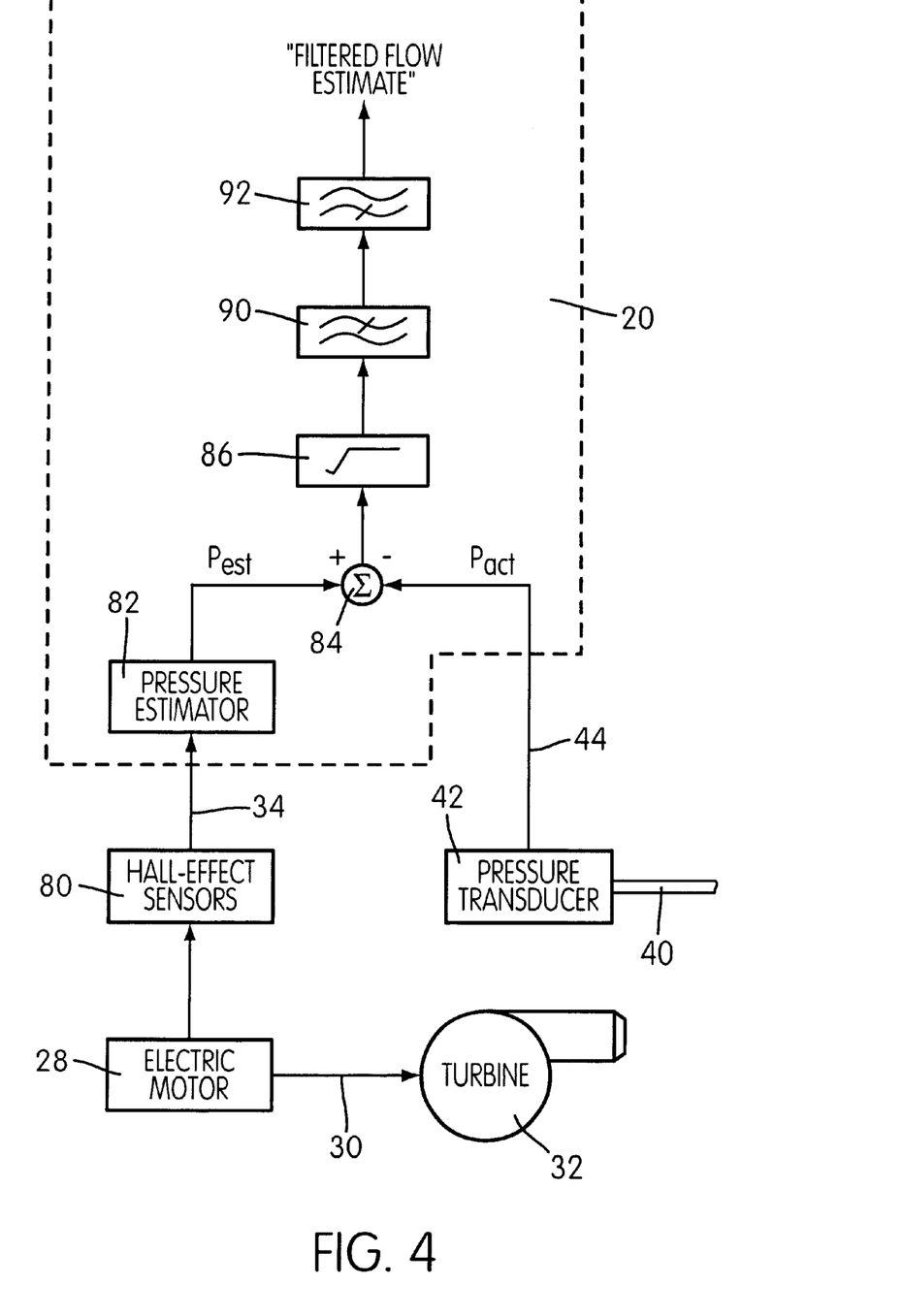
FIG. 4 is a schematic block diagram relating to FIG. 3.

A method of flow estimation now will be described with reference to FIGS. 3 and 4. As would be apparent to one skilled in the art, the processing to be described can readily, be implemented by way of a computer program. In the first step 60, the motor speed is measured by means of the motor's Hall-effect sensors 80. From this rotational speed value, the equivalent pressure. $p_{est}$, that would be developed by the turbine 32 for that measured speed if the flow were zero is estimated in step 62 by means of the pressure estimator 82, using a predetermined mathematical function.

One method of estimating the equivalent pressure, $p_{est}$, is to apply the motor speed as the input to a quadratic function, having the form:

$$p_{est}=c_1\omega^2+c_2\omega+c_3 \tag{1}$$

where $c_1$, $c_2$ and $C_3$ are constants, which may take any value including zero, derived from previously determined pressure/speed characteristics of the turbine 32, and $\omega$ is the motor speed. On the basis of the applicant's Sullivan™ III machine as described. representative co-efficient values are $c_1=118$, $c_2=0$ and $C_3=0$. The coefficients were calculated using a linear regression technique on the pressure/speed data for zero flow of the Sullivan™ III apparatus. The impedance of any inlet baffle and the pneumatic circuit of the turbine affect the coefficients.

In an alternative implementation, a higher order polynomial may be used to estimate the equivalent pressure, for zero flow, from motor speed, motor current and/or armature voltage.

In another alternative implementation, a lookup table may be used to estimate the equivalent pressure for zero flow from motor speed, motor current and/or armature voltage based on an empirical set of measurements.

Coincidentally the speed measurement and pressure estimation with pressure steps 60,62, the delivery tube pressure, $p_{act}$ is measured in step 64 by means of the pressure transducer 42, and $p_{act}$ together with $p_{est}$ are passed to a differential summation device 84 whereby, in step 66, the difference between the two pressures is calculated. The output from the summation device 84 represents an estimation of flow $f_{est}$.

A conventional orifice plate meter consists of a thin plate which is inserted into the air-delivery, tube. The plate has a central orifice that is smaller than the diameter of the tube and ports either side of the plate for measuring pressure. The obstruction results in a constriction of the flow and a local pressure disturbance which can be measured. The flow q is determined by measuring the pressure at the sensing ports and is given by $$q = c\sqrt{p_1 - p_2} \quad (2)$$

where c is a constant for a given configuration, $p_1$ is the pressure at the sensing port preceding the orifice plate and $p_2$ is the pressure at the sensing port following the plate.

As previously noted, measurement of both pressure and flow in a CPAP machine usually requires at least two transducers. A pressure transducer is required for pressure regulation and a second transducer is required for flow measurement. The second transducer may be either a pressure transducer or a flow transducer. In the first case flow is given by equation (2), in the later case flow is measured directly.

For non-zero flow, it is seen from equation (2) that the pressure $p_1$ is greater than $p_2$ remains constant.

At zero flow, the pressures $p_1$ and $p_2$ are equal and can be estimated from a quadratic function of the motor speed having the form of equation (1).

For non-zero flow, $p_1$ is increased, to meet the increased flow, by increasing the motor speed. Therefore, the pressure estimate derived from the motor speed also increases. The change in motor speed is approximately proportional to the change in flow, then the change in $p_{est}$ is proportional to the change in $p_1$. The flow $\hat{f}_{est}$ can be estimated, therefore, from the difference between the pressure estimate $p_{est}$ and the measured pressure $p_2$, ie.

$$\hat{f}_{est} = c\sqrt{p_{est} - p_2} \quad (3)$$

The orifice plate 52 has a 'square law' impedance, in which case the output of the summation device 84 represents "FLOW SQUARED". In such a case, the "FLOW SQUARED" value can be linearised in step 68 by the square root device 86, and then filtered in step 70 by the combination of low pass and high pass filters 90,92 to derive a "FILTERED FLOW ESTIMATE" value, that has the non-respiratory components removed. The low pass filter preferably will have an upper frequency limit of 20 Hz to remove noise, while the high pass filter preferably will have a lower frequency limit of 0.1 Hz to remove non-respiratory components.

Flow Compensation

The performance of flow compensation, which enables flow induced pressure swings at the mask to be minimised, will now be described with reference to FIG. 5. The method of flow compensation can be utilised using the flow estimation value calculated in accordance with the method described above, or on the basis of a flow measurement made by a flow transducer.

In a preferred embodiment, the flow-generator incorporates a pressure transducer used for pressure regulation such as shown in FIG. 1. The transducer 42 measures pressure in the gas delivery circuit at a point removed from the mask. The flow induced pressure perturbations at the mask are therefore larger than that at the controlled point. The compensation of flow-induced pressure perturbations at the mask is by way of compensating control over the mask pressure, while still retaining adequate flow for respiration purposes.

Figure 5:
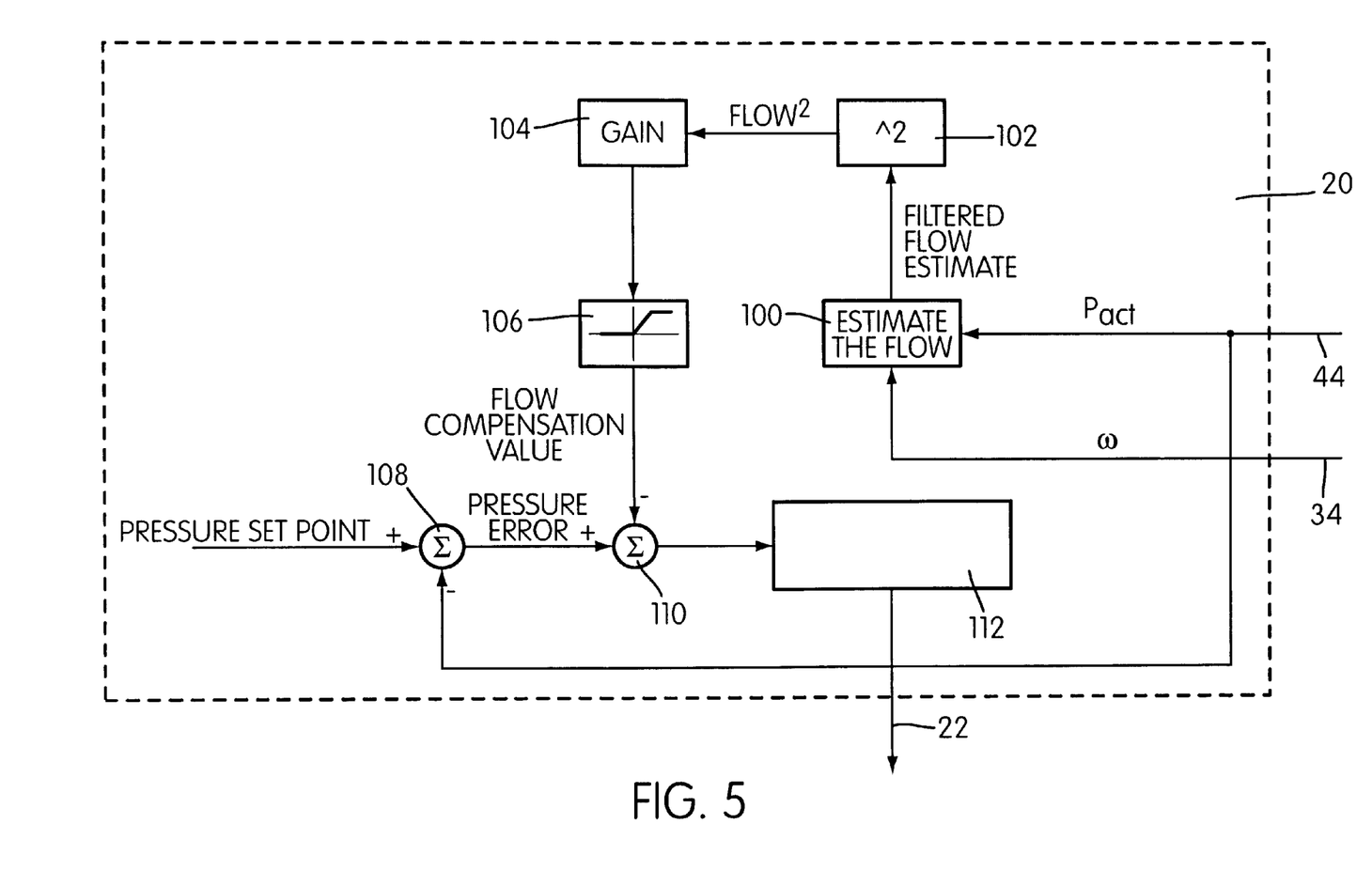
FIG. 5 is a schematic block diagram relating to the compensation of flow-induced pressure swings.

FIG. 5 shows the processing performed by the motor controller 20 in performance of the flow compensation. As would be apparent to one skilled in the art, the function of the logical blocks can be implemented by way of a computer program. Both the electric motor speed and the actual measured delivery pressure are provided to a computational element 100 respectively by the signal lines 34 and 44. The computational element 100 estimates the flow in accordance with the technique described in conjunction with FIGS. 3 and 4, thus the output of the computational element is the "FILTERED FLOW ESTIMATE". That signal is passed to a squarer element 102 to derive a signal representing "FLOW$^2$". In the alternative, where the orifice plate used to derive delivery pressure is a square-law type, then, as previously described, an estimate of "FLOW$^2$" is obtained directly in the flow estimation method, hence the squaring function of the squarer element 102 need not be performed. The estimated "FLOW$^2$" value is passed to a gain element 104 that scales the signal. The scale factor may take on any value, including one and zero, may have a positive or negative sign and may take on different values at different times. In a typical implementation, that incorporates an obstruction of the air-delivery circuit, the scale factor is zero for negative flow, ie when the mask pressure is less than the pressure at the turbine, and a small positive constant, less than one, when the flow is positive.

The scaled flow signal passes by a limiter element 106, the function of which is to limit the magnitude of the "FLOW COMPENSATION VALUE" to a predetermined value to ensure stability.

By way of further explanation, when pressure is measured from within the recirculation region 54, and is the controlled variable, the mask pressure initially increases with increasing flow and then falls. The deviation from the pressure set point can be reduced, therefore, by subtracting the scaled flow estimate from the pressure set point. However, if the estimated flow is negative (i.e, the measured pressure is greater than the estimate pressure), no compensation is implemented to avoid instability due to positive feedback.

As the mask pressure varies as the square of flow, the flow compensation technique can be refined by making the compensation value proportional to the square of flow. Beyond a certain flow value, the mask pressure will begin to fall with increasing flow. It may be desired, therefore, to limit the magnitude of the compensation value. The most preferable limit would be at the turning point of the pressure/flow curve. The turning point is variable and is a function of motor speed. Alternatively, and more simply, a fixed limit could be used.

The constants in equation (1) can be calculated from recorded pressure/speed data at zero flow. For the purposes of flow compensation, the value of the constant in equation (3) may be unimportant (as it is replaced by a scaling factor), however, if required, it may be derived by fitting equation (3) to measured flow data. The complete flow compensation procedure is as follows:

1. calculate $p_{est}$ from equation (1),
2. measure the pressure $p_2$,
3. calculate the compensation value ($p_{est}-p_2$), which is proportional to flow squared,
4. if the compensation value is negative set the compensation to zero,
5. multiply the compensation value by the scale factor,
6. limit the magnitude of the compensation value, and
7. subtract the flow compensation from the pressure error.

The control loop minimises the difference between the set pressure and the measured pressure, and at the same time minimises the difference between the pressure that should be generated for the measured motor speed and the measured pressure.

The outputs from the limiter element 106 represents the "FLOW COMPENSATION VALUE" scaled in accordance with the pressure-controlling signals. The "PRESSURE SET POINT" is compared with the measured pressure at the differential summation element 108, generating a "PRESSURE ERROR" signal. The "PRESSURE ERROR" signal and the "FLOW COMPENSATION VALUE" form the inputs to a further differential summation element 110, and in this way the control variable of "TREATMENT PRESSURE ERROR" is compensated in accordance with flow, the output from the summation element 110 passing to a controller unit 112 that provides the controlling signal to the motor power supply 24 on the control line 22.

The set point pressure may not be the mask pressure, as is the case for the arrangement shown in FIG. 1, where it is the turbine output pressure that is measured. In that case, the pressure set point has been pre-compensated by the controller unit 112 to be in relation to the point where pressure actually is measured relative to the desired mask CPAP treatment pressure.

Figure 6:
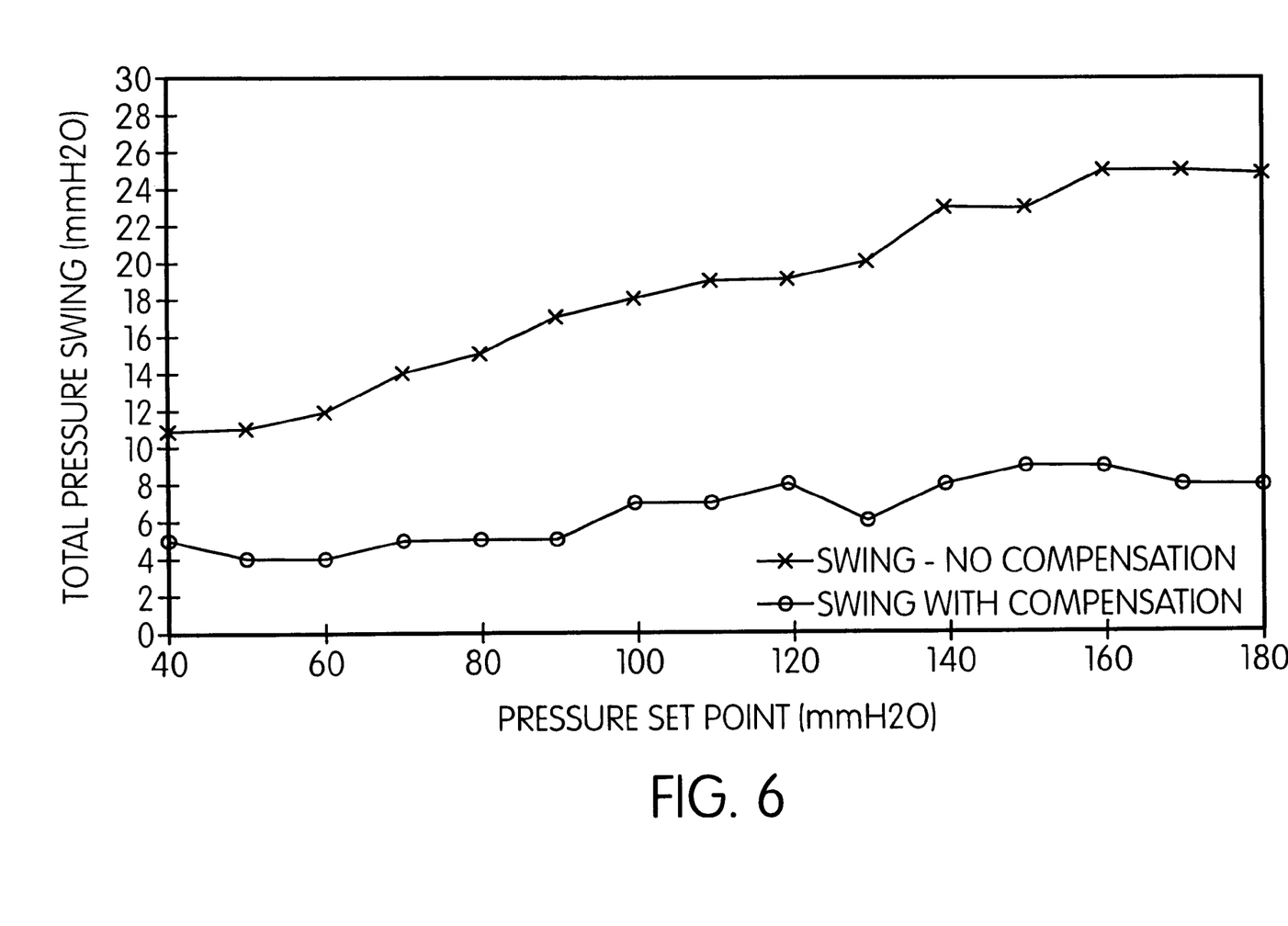
FIG. 6 is a chart of pressure swing versus set-point (treatment) pressure.

In tests of the flow compensation methodology described utilising the CPAP apparatus described above, for a set mask treatment pressure of 10 cm $H_2O$, the magnitude of the pressure swings without compensation was 1.8 cm $H_2O$. With flow compensation in place, the swings are reduced to 0.7 cm $H_2O$. Over the range of 4–18 cm $H_2O$, the average reduction in the magnitude of the pressure swing at the mask reduced by respiratory flow was 64%. The data is shown in FIG. 6.

What is claimed is:

1. A method to estimate the flow of breathable gas to a patient from a flow generator having a turbine in the administration of continuous positive airway pressure (CPAP) treatment or assisted respiration, the method comprising:

measuring a pressure of gas ($P_{act}$) delivered by the flow generator;

measuring a rotational speed ($\omega$) of the turbine;

estimating a pressure of gas ($P_{est}$) delivered by the flow generator at the measured rotational speed ($\omega$) if there were no flow to the patient; and calculating the difference between $P_{est}$ and $P_{act}$ to give an estimate of the flow to the patient ($f_{est}$).

2. A method as claimed in claim 1, further comprising taking the square root of the flow estimate to provide a linearized flow estimate.

3. A method as claimed in claim 2, further comprising filtering said linearized flow estimate to remove non-respiratory components.

4. A method as claimed in claim 1, whereby said estimating comprises performing the calculation:

$$P_{est}=C_1\omega^2+C_2\omega+C_3$$

where $C_1$, $C_2$ and $C_3$ are known constants.

5. A method as claimed in claim 1, whereby the step of estimating comprises reviewing tabulated incremental rotational speeds with predetermined values of pressure for no flow to identify the relevant value of $p_{est}$.

6. An apparatus for estimating the flow of gas from a flow generator having a turbine, and supplying breathable gas in the administration of CPAP treatment or assisted respiration, the apparatus comprising:

pressure measurement device for measuring the pressure of gas from the flow generator when operating at a known turbine rotational speed;

pressure estimation device for estimating the pressure of gas that would be delivered by said flow generator at the known rotation speed if there was no flow; and a processor for calculating the difference between the measured pressure and the estimated pressure to give an estimation of flow.

7. An apparatus to provide CPAP treatment or assisted respiration by the supply of a positive treatment pressure of breathable gas to a patient's airway, the apparatus comprising:

a flow generator having a turbine;

a gas delivery tube connected at one end thereof with the flow generator;

a patient mask adapted to be worn by a patent connected to the other end of the delivery tube;

a pressure sensor sensing delivery pressure from either the flow generator or the delivery tube remote from the mask; and a processor for controlling the flow generator, and further programmed to estimate the flow of breathable gas to the patient by estimating the pressure of gas that would be delivered by the flow generator at the actual turbine rotational speed for zero flow and calculating the difference between the measured pressure and said estimated pressure to give said estimate of flow, said estimate of flow being utilized by the processor to dynamically adjust a control signal provided to said flow generator to reduce flow-induced pressure swings at the mask.

8. A method to reduce flow-induced pressure swings at a patient mask during the administration of CPAP treatment or assisted respiration, said mask being coupled by a gas delivery tube to a flow generator having a turbine, and the pressure of delivered gas being measured at a point remote from said mask, said measured pressure used to derive a treatment pressure control signal supplied to said flow generator to control said desired treatment pressure, the method comprising:

determining a flow of gas to the patient including measuring the rotational speed ($\omega$) of the turbine, estimating the pressure of gas ($P_{est}$) that would be delivered by the flow generator at the measured rotational speed ($\omega$) if there were no flow to the patient, and calculating the difference between $P_{est}$ and $P_{act}$ to give the estimate of the flow to the patient ($F_{est}$);

scaling said determined flow; and adjusting said treatment pressure control signal by said scaled flow.

9. A method as claimed in claim 8, further comprising filtering said scaled flow to pass only the scaled flow corresponding to increases in flow that correspond to a reduction in treatment pressure.

10. A method as claimed in claim 8, said estimating comprises performing the calculation:

$$P_{est} = C_1 \omega^2 + C_2 \omega + C_3$$

where $C_1$, $C_2$ and $C_3$ are known constants.

11. A method as claimed in claim 10, estimating comprises obtaining the incremental rotational speed which corresponds to a pressure for no flow to identify the relevant value of $P_{est}$.

* * * * *